United States Patent [19]

VanPelt et al.

[11] Patent Number: 4,550,422
[45] Date of Patent: Oct. 29, 1985

[54] PROCESS AND DEVICE FOR X-RAY SYSTEM QUALITY ASSURANCE

[75] Inventors: Wilbur F. VanPelt; Richard W. Peterson, both of Seattle, Wash.

[73] Assignee: The United States of America as represented by the Department of Health and Human Services, Washington, D.C.

[21] Appl. No.: 440,728

[22] Filed: Nov. 10, 1982

[51] Int. Cl.$^4$ .......................... G01T 1/16; H05G 1/26
[52] U.S. Cl. ...................................... 378/207; 378/210
[58] Field of Search ....................... 356/443, 444, 243; 378/207

[56] References Cited

U.S. PATENT DOCUMENTS

| | | |
|---|---|---|
| 1,953,471 | 4/1934 | Eich . |
| 2,053,317 | 9/1936 | Billing . |
| 2,258,593 | 10/1941 | Black .................................. 378/207 |
| 2,322,044 | 6/1943 | McFarlane et al. ................. 356/443 |
| 2,326,007 | 8/1943 | Capstaff . |
| 2,379,814 | 7/1945 | McFarland ........................... 378/62 |
| 2,460,060 | 1/1949 | Butler . |
| 2,799,581 | 7/1957 | Bullock . |
| 3,864,038 | 2/1975 | Palazzolo .............................. 355/40 |

OTHER PUBLICATIONS

Clark, G. L., The Encyclopedia of X-Rays, and Gamma Rays, Reinhold, New York, 7/63, p. 380.

Primary Examiner—Alfred E. Smith
Assistant Examiner—T. N. Grigsby
Attorney, Agent, or Firm—Browdy and Neimark

[57] ABSTRACT

A method and apparatus for evaluating the performance of diagnostic x-ray systems. The method consists of using an x-ray generator under standard conditions and making a test x-ray film, for example, of the dental intra-oral type and comparing its density with a calibrated step density strip, using a test tool member consisting of a sleeve-like body with opaque parallel flat top and bottom walls receiving the step density strip slidably therebetween. The flat walls have registering transverse rectangular windows, in the forward parts of which can be exposed a selected density step. The rear portion of the body, between the flat walls, has spacer blocks defining therebetween a transverse channel overlapped by the windows through which the test x-ray film can be inserted to compare its density with that of the selected step density. This can be utilized to determine if the test film density is within an optical density in a desired range including certain steps of the calibrated density strip. The step density tablet can have steps ranging from 0.7 optical density to 1.5 optical density. A metal filter plate may be mounted on one end portion of the tool body of a thickness selected to match the output of the x-ray generator to the response of the film so as to produce a test film of optical density of about 1.00 O.D. when the x-ray system is known to operate satisfactorily.

13 Claims, 9 Drawing Figures

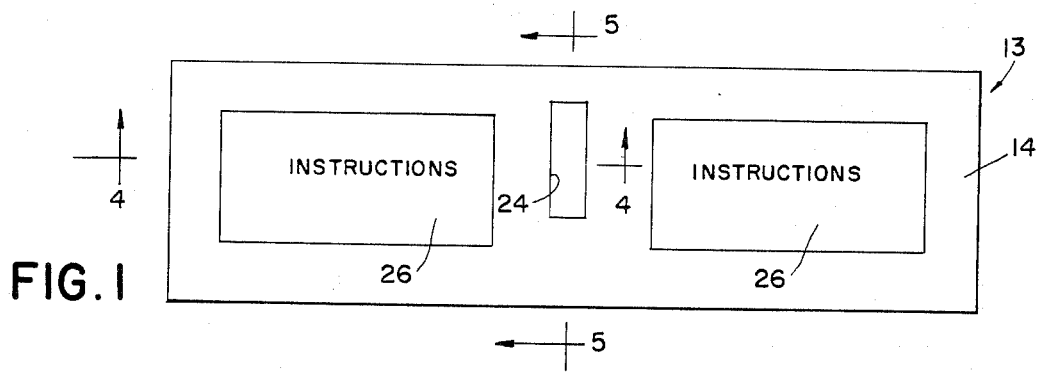
FIG. 1
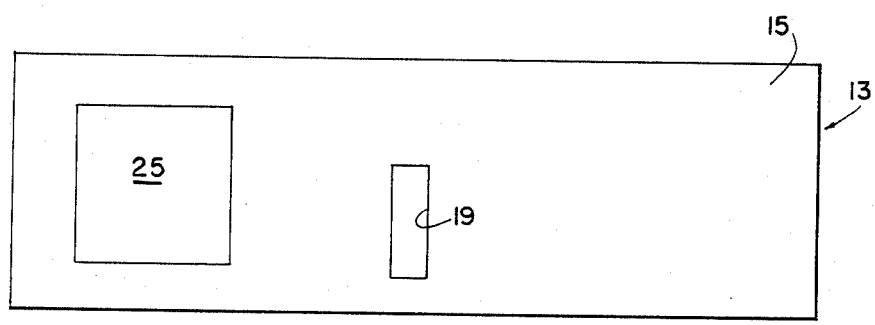
FIG. 2
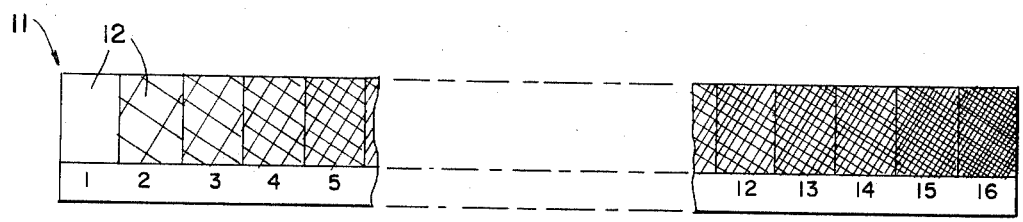
FIG. 3
FIG. 4
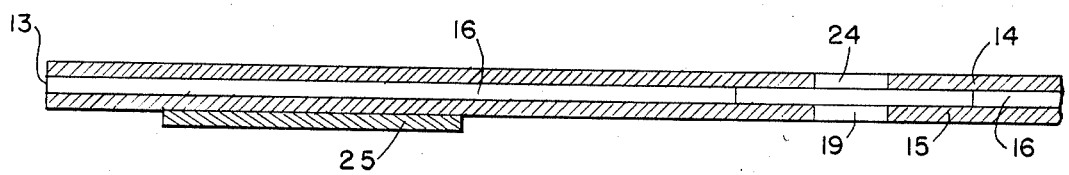
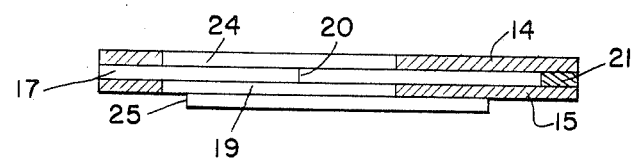
FIG. 5

PROCESS AND DEVICE FOR X-RAY SYSTEM QUALITY ASSURANCE

FIELD OF THE INVENTION

This invention relates to medical radiography test systems, and more particularly to a method and apparatus for providing evaluation of a medical or dental x-ray system consisting of x ray generator, film and processor on a daily basis and to thereby assure the production of useful radiographs from the system with no need to repeat patient exposure because of problems with the x-ray system.

BACKGROUND OF THE INVENTION

Existing x-ray film sensitometry typically uses an expensive combination of sensitometer and densitometer to evaluate the operation of film processing. The sensitometer (which costs from $250 to $650) produces three to twenty-one different exposures on a test film which is then processed in a facility's processor. The densitometer (which costs from $300 to $1000) evaluates the densities on the film to determine any changes from standard. Such changes can indicate a failure of an x-ray imaging/processing system which would possibly result in either excess exposure of a patient to radiation, to produce a useful radiograph, or would subject the patient to radiation exposure without yielding desired information on the radiograph. This process is currently used in larger x-ray facilities and does produce excellent results in the maintenance of daily quality control. The method does, however, require the expenditure of about $1000 to begin with, requires storage space, record keeping, and graphing of results, as well as considerable training of operating personnel.

Another approach is generically different from the above-described approach and results in simplification. The sensitometer is dispensed with and the x-ray generator is used to produce an exposure on a test film through a step wedge, usually a machined aluminum block producing 3-15 densities on the film. After processing, the test film may either be analyzed with a densitometer or by visual comparison with another similar 3-15 density step master film. Changes in the density of th steps of the test film from those of the master film indicate a possible problem. This approach affords significant improvement by providing monitoring of both the reproducibility of the performance of the x-ray apparatus and the x-ray imaging/processing system.

This last-named process is simple, but is difficult to apply directly to dental x-ray film (as done in standard sensitometry first-described above), since the films are so small as to preclude easy production or analysis of stepped images. Additionally, step wedge imaging requires an exposure different from that in typical use on patients and would not test system operation at patient use settings. Visual comparison of the step wedge images is difficult since the eye is called upon to make a match under distracting, confusing conditions, of numerous shades of image.

One comparison device, marketed by the Spectronics Corporation, would have exposures to a test film made under a standard condition and the test films compared to a standard control film. This assumes that there is an optimum condition that is suitable to all dentists, and the instructions on the Spectronics Corp. device assume that if the test film does not turn out light or dark enough, the exposure should be changed. This does not address the issue of controlling film processing, which is usually the major variable in system response.

A preliminary search of the prior art revealed the following prior U.S. patents of interest:

| Eich,     | 1,953,471 |
| Billing,  | 2,053,317 |
| Capstaff, | 2,326,007 |
| Butler,   | 2,460,060 |
| Bullock,  | 2,799,581 |

SUMMARY OF THE INVENTION

The test tool employed in the present invention uses the x-ray generator to produce a single density on a film. The generator is first tested to assure that it is reproducible in radiation output. (Survey results indicate that the x-ray machine itself is typically reproducible.) Filters attached to the test tool are used to alter the x-ray beam, produced at normal patient use settings, so as to produce an exposure on film which is in the optical density range of 0.8-1.2, the most-used density range on film. The test tool contains an optical density comparison step tablet which is adjusted to match the density of the test film. The tool is so designed as to compare the density of the test film against one comparison density at a time and to screen the eye against other confusing background densities, to make comparison more accurate. Instructions are provided on the test tool for adjusting the processing parameters rather than adjusting exposure. The test tool is a single device which includes (1) the necessary filter, (2) the step tablet, and (3) the instructions, all on one device. The steps on the comparison step tablet differ in density by approximately 0.1 Optical Density, and the variance of 0.2 O.D. or more from a chosen standard is typically recognized as the usual limit of variability in processing.

Accordingly, a main object of the present invention is to provide an improved method and means for the evaluation of an x-ray system which overcomes the disadvantages and deficiencies of the previously employed x-ray system performance-evaluating systems.

A further object of the invention is to provide an improved x-ray system performance evaluation system which enables evaluation of an x-ray system on a daily basis and to thereby assure the production of useful radiographs therefrom without the need for repeating patient exposure because of deficiencies of the x-ray system.

A still further object of the invention is to provide an efficient x-ray machine evaluation system which employs an inexpensive test tool and does not require costly additional apparatus in measuring the performance of an x-ray system.

A still further object of the invention is to provide an improved system for evaluating the performance of an x-ray system which can be carried out by relatively unskilled personnel, which gives accurate results, which can be easily used on a daily basis with very small expense, and which requires very little storage space, record keeping, or complex analysis of results, as well as requiring minimal training of operating personnel.

A still further object of the invention is to provide an improved system for evaluating the performance of a dental x-ray system by employing a sample conventional dental x-ray film to receive an exposure from the machine through an appropriate filter element, and then comparing the density of the developed test sample film with a master step wedge film carrying graduated known-density areas which can be moved into registry with the developed test sample film for optical comparison, the system including a novel test tool which facilitates the visual comparison of the developed test sample film with the calibrated step densities of the master step wedge film.

BRIEF DESCRIPTION OF THE DRAWINGS

Further objects and advantages of the invention will become apparent from the following description and claims, and from the accompanying drawings, wherein:

FIG. 1 is a top plan view of the main body portion of a test tool employed in an x-ray system evaluating system according to the present invention.

FIG. 2 is a bottom plan view of the test tool main body portion of FIG. 1.

FIG. 3 is a plan view of an optical density-calibrated step wedge film strip employed with the test tool main body portion of FIGS. 1 and 2.

FIG. 4 is an enlarged longitudinal vertical cross-sectional view taken substantially on line 4—4 of FIG. 1.

FIG. 5 is an enlarged transverse vertical cross-sectional view taken substantially on line 5—5 of FIG. 1.

DETAILED DESCRIPTION OF A PREFERRED EMBODIMENT

Figure 6:
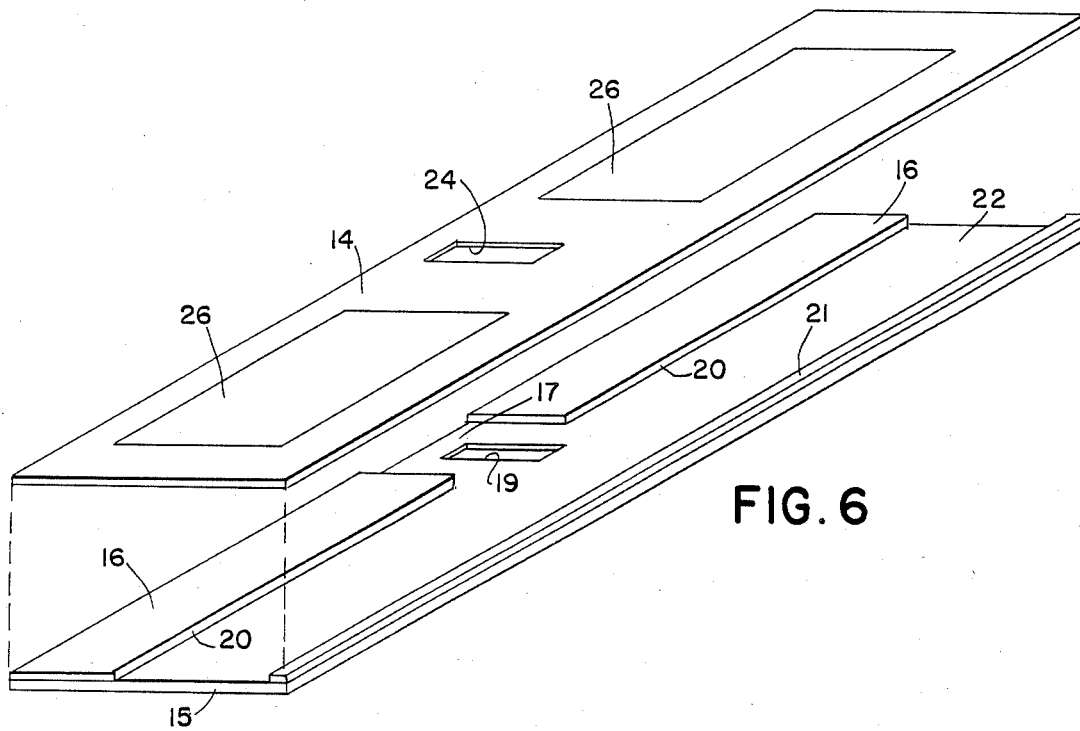
FIG. 6 is an enlarged perspective view of the major components of the test tool main body portion of FIGS. 1 and 2, shown in separated positions.

The test tool used in the above-described film exposure feasibility determination is designed to accommodate conventional dental x-ray film of the intra-oral type (for example, ANSI-type, Size No. 12). However, any film configuration may be employed, provided that it conforms with the main body of the test tool, presently to be described, namely, a substantially flat sleeve-like member having optically opaque, spaced parallel flat top and bottom walls rigidly secured together at their longitudinal margins and provided with (1) a passage defining a transverse channel to slidably receive a step tablet strip such as that shown in FIG. 3, (2) an opening to allow for the inspection of the dental test film, and (3) an arrangement to allow accurate optical comparison of the test film with the step tablet densities (see FIG. 7). An important feature is that the test film opening is designed to concurrently allow the display of the test film with only one step tablet density at a time, so as to preclude distraction of the viewer's eye. Suitable instructions for use are therefore preferably provided on the main body of the test tool.

Referring to the drawings, and more particularly to FIG. 3, the optical density step tablet, shown generally at 11, (which can be made either photographically or radiographically) comprises an elongated film strip provided with graduated-density segments 12, said film strip segments having optical densities which may range from a low density value of about 0.7 O.D. to about 1.5 O.D. in steps of approximately 0.1 O.D., although this may be varied in accordance with the nature of the intended application. The density range is preferably selected around the typical response of x-ray film and the definition point for film speed of 1.0 O.D. plus base and fog densities. The step tablet segments may be labelled in terms of arbitrary step numbers, as shown in FIG. 3, or alternatively, in terms of measured optical density.

Figure 7:
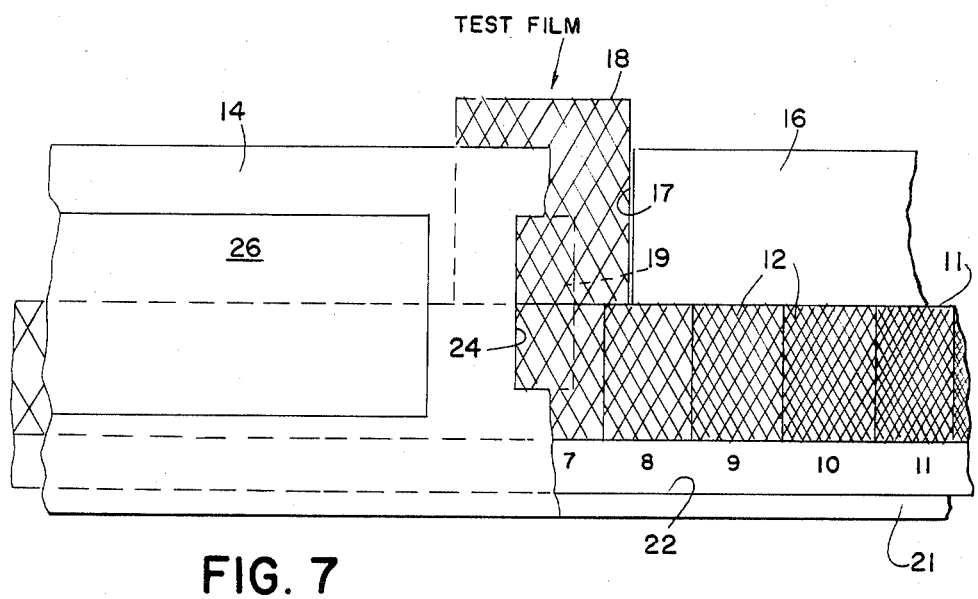
FIG. 7 is an enlarged fragmentary top plan view, with parts broken away, of the central portion of the assembled test tool, shown in operating position.

Referring to FIGS. 1, 2, 4 and 5, the test tool main body is designated generally at 13. Main body 13 comprises a substantially flat, elongated, rectangular sleeve formed of optically opaque material having a top wall 14 and a spaced, parallel bottom wall 15. As shown in FIG. 6, bottom wall 15 is provided at one longitudinal margin with symmetrically arranged spacer blocks 16, 16 integrally made or otherwise rigidly secured thereon, extending longitudinally from the opposite ends of said bottom wall and spaced from each other at their inner ends to define a transverse channel 17 adapted to slidably receive a conventionally shaped test film 18, as shown in FIG. 7. Centrally of said channel 17, bottom wall 15 is formed with a transversely extending slot 19, about half of the slot lying in said channel and the remaining half extending forwardly beyond the longitudinal inner edges 20, 20 of the spacer blocks 16, 16.

The forward longitudinal margin of bottom wall 15, as viewed in FIG. 6, is provided with a rigidly-secured, full length, narrow upstanding spacer strip 21, of the same thickness as and cooperating with the rear spacer blocks 16, 16 to define a longitudinal channel 22 shaped to slidably receive the density step tablet 11.

The top wall 14 is formed with a transverse slot 24 identical to and in vertical registry with slot 19. Top wall 14 is rigidly secured on spacer blocks 16, 16 and spacer strip 21 in spaced parallel relation to and registering with bottom wall 15.

Figure 9:
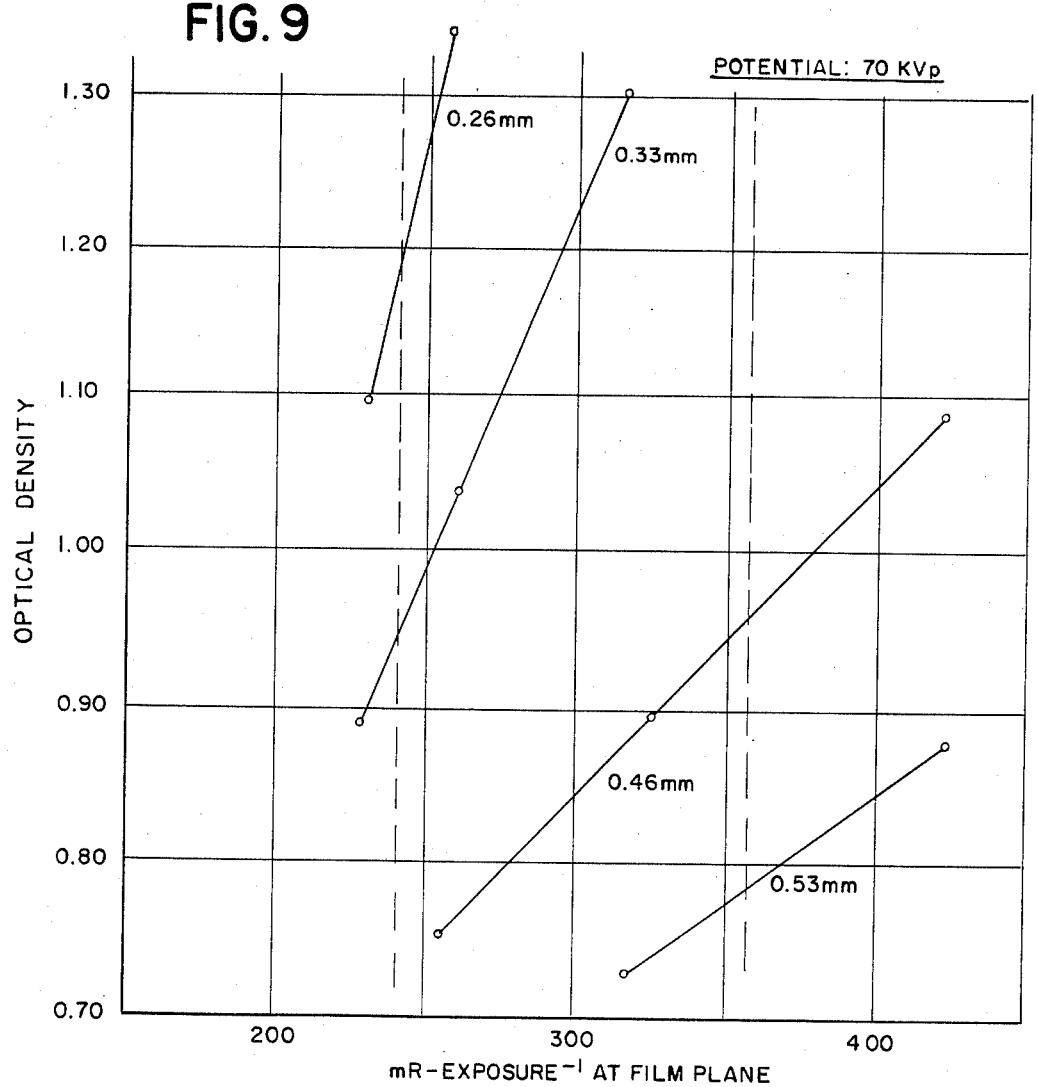
FIG. 9 is a graph showing typical test film optical density results for an x-ray generator, using exposure-attenuating filters of different thicknesses, as a function of measured radiant energy outputs from the x-ray machine received at the film plane.
Figure 10:
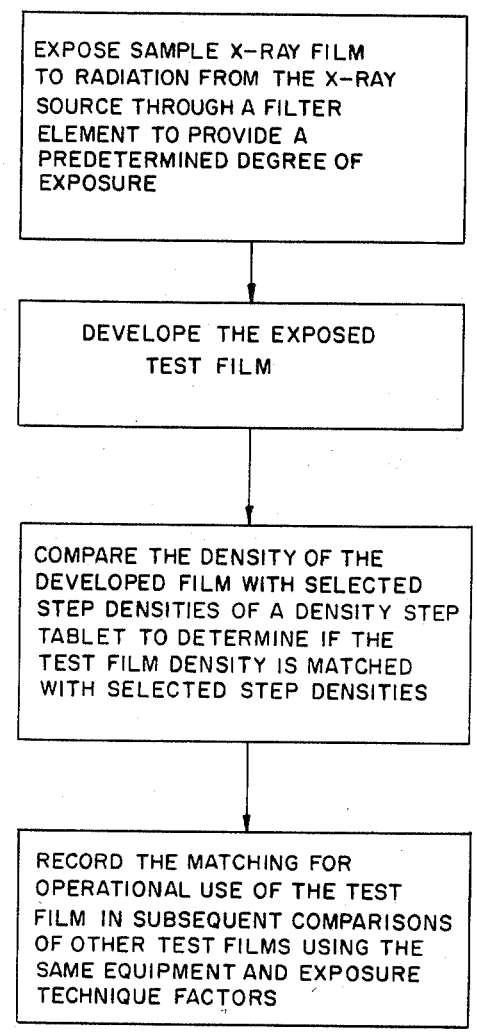
Figure 11:
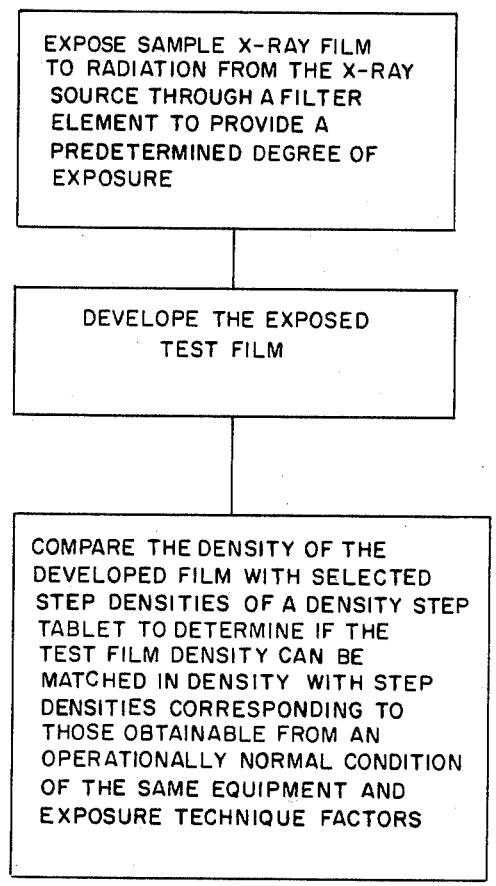

A suitable x-ray filter plate 25, such as a thin copper plate, is secured to one end portion of bottom wall 15, as shown in FIGS. 2, 4 and 5. The thickness of the filter plate is chosen on a facility-by-facility basis, to match the output of the x-ray generator to the response of the test film in use, so as to produce a test film optical density of about 1.0 O.D. when the x-ray system to be monitored is known to be operating satisfactorily. A suitable chart may be provided, for example, such as shown in FIG. 9, which may be employed to assist in determining the actual filter thickness to be used, as based on the measured output of the x-ray generator at a known input potential. Alternatively, a series of filters, furnished with each tool could be used without radiation measurement to empirically determine an appropriate match.

Suitable instruction labels 26 may be provided on the top face of wall 14, as shown in FIGS. 1 and 6.

The provision of the registering top and bottom slots 24, 19 allows the density comparison to be made by light transmitted through bottom slot 19 from any suitable light source located to illuminate said bottom slot. As shown in FIG. 7, the width of the transverse comparison slots 24, 19 is preferably considerably less than the widths of the optical density segments 12 to facilitate the concurrent display of the test film 18 with only one segment 12 at a time.

The test tool has both a preparatory, or "set-up", cycle and an operational cycle. The set-up cycle consists of recording the usual patient x-ray exposure technique factors (kilovoltage, milliamperage, and time) on the body 13 at specified locations thereon. The test film exposure is made at a fixed distance between the x-ray origin and a reference surface 30, as illustrated diagrammatically in FIG. 8. If a measurement of radiation exposure can be made at said fixed distance, the results of that measurement can be used in conjunction with an appropriate chart for the potential employed, such as that shown, for example, in FIG. 9, to determine the proper thickness of filter 25.

Figure 8:
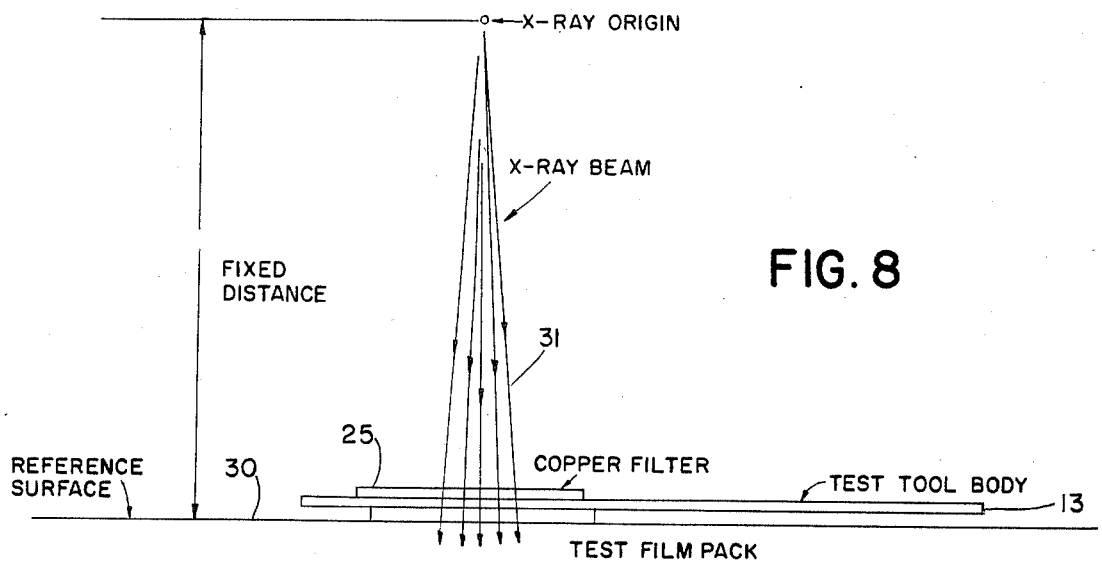
FIG. 8 is a diagram substantially showing the position of the test tool relative to the x-ray source in making a test x-ray exposure of a sample dental film at the beginning of an x-ray system evaluation process according to the present invention.

In exposing the test film 18, the test film, enclosed in a light-tight container, such as the normal cardboard or plastic wrapper on a dental film, is placed on an appropriate selected surface 30 at the above-mentioned fixed distance from the x-ray origin. The body 13 of the test tool is placed on the film pack, with a filter 25 placed thereon, as shown in FIG. 8, the filter 25 and film pack being aligned with the path of the x-ray beam, shown at 31, so that the beam 31 must pass through the filter 25 and body 13 before reaching the film. A single exposure is made at the selected technique factors, the test film 18 is processed in a normal manner, and the developed test film 18 is then inserted into the test tool body via the transverse channel 17.

With the step tablet 11 in the longitudinal channel 22 and the inner edge of the test film 18 slidably abutting the longitudinal edge of the step tablet 11, the step tablet is adjusted longitudinally so that a visual comparison can be made against the densities of the step table segments 12. If the matching density is approximately mid-range on the step tablet, the match step is recorded and the filter 25 is permanently attached to the test body 13. (If no x-ray output exposure value is capable of being obtained, a selection of filters is used to experimentally determine the appropriate match). The now-calibrated test tool is then ready for operational use, and can be turned over to the dental facility.

In operational use, the user periodically places a test film pack on a selected surface 30 at the required fixed distance from the x-ray origin, covers the film pack with the filter end of the test tool, as shown in FIG. 8, preferably employing a suitable position-indicating device to assure the fixed exposure distance, and makes an x-ray exposure at the selected technique factors (kilovoltage, milliamperage, and time). The test film 18 is developed using the facility's normal procedure, and inserted into the transverse channel 17 of the test tool body 13. The test film 18 and step tablet 11 are then matched. If the match is off by two steps or more, the facility is directed to take the necessary steps to correct the situation. (Corrective action may consist of correcting the processing operation, or calling a service technician to service the x-ray machine.

While specific embodiments of a method and apparatus for providing evaluations of x-ray systems have been disclosed in the foregoing description, it will be understood that various modifications within the scope of the invention may occur to those skilled in the art. Therefore it is intended that adaptations and modifications should and are intended to be comprehended within the meaning and range of equivalents of the disclosed embodiments.

What is claimed is:

1. An x-ray generator test tool comprising housing means formed of optically opaque material having a top wall and a spaced parallel bottom wall, means defining a linear channel between said walls, an optical density step tablet slidably disposed in said linear channel and having a plurality of successive step segments graduated in optical density, means defining a transverse channel extending from one edge of said housing means perpendicular to and communicating with said linear channel, said transverse channel being adapted to receive a test film for comparison with said optical density step segments, means defining light-transmitting windows in said housing means simultaneously exposing said linear and transverse channels at the region where the transverse channel communicates with the linear channel, and x-ray filter means comprising a thin copper plate secured on one of said walls and for filtering clinical x-ray kilovoltages of 70 kV-100 kV mounted on said housing means at a non-interfering location relative to said windows.

2. The test tool of claim 1, and wherein said windows comprise registering apertures formed in said top and bottom walls.

3. The test tool of claim 1, and wherein said windows comprise registering transverse slots formed in said top and bottom walls.

4. The test tool of claim 1, and wherein said housing means is in the form of a substantially flat elongated sleeve.

5. The test tool of claim 4, and wherein said transverse channel is substantially at the midportion of said elongated sleeve.

6. The test tool of claim 1, and wherein said windows are of lesser width than said optical density step segments.

7. The test tool of claim 1, and wherein said windows comprise registering transverse slots formed in said top and bottom walls and exposing adjacent portions of said transverse and linear channels.

8. The test tool of claim 1 wherein said filter means comprise means for matching the output of the x-ray generator to the response of the test film used.

9. The test tool of claim 1 wherein said x-ray filtered means is of sufficient thickness so as to result in an optical density of about 1.0 on film when the film is exposed to a beam of x-radiation generated at typical clinical x-ray kilovoltages of 70 kV–100 kV, said beam having passed through said copper plate.

10. A method of evaluating the performance of an x-ray system comprising exposing a sample conventional x-ray film, used as a test film, to radiation from the x-ray generator at predetermined exposure technique factors through a filter element selected to normally provide a predetermined degree of exposure, developing the exposed test film, comparing the density of the developed test film with selected step densities of a density step tablet to determine if the test film density is matched with said selected step densities, and recording the matching for operational use of the test film in subsequent comparisons using other test films obtained from the same x-ray generator under the same exposure technique factors and using the selected filter element in the x-ray transmission path between the x-ray generator and said other test films.

11. A method of evaluating the performance of an x-ray system as set forth in claim 10, wherein the step of comparing the density of the developed test film is carried out using an x-ray system test tool comprising housing means formed of optically opaque material having a top wall and a spaced parallel bottom wall, means defining a linear channel between said walls, an optical density step tablet slidably disposed in said linear channel and having a plurality of successive step segments graduated in optical density, means defining a transverse channel extending from one edge of said housing means perpendicular to and communicating with said linear channel, said transverse channel being adapted to receive a test film for comparison with said optical density step segments, means defining light-transmitting windows in said housing means simultaneously exposing said linear and transverse channels at the region where the transverse channel communicates with the linear channel, and x-ray filter means mounted on said housing means at a non-interfering location relative to said windows.

12. A method of evaluating the performance of an x-ray system comprising exposing a conventional x-ray film, used as a test film, to radiation from the x-ray generator at predetermined exposure technique factors through a filter element selected to normally provide a predetermined degree of exposure, developing the exposed test film, and comparing the density of the developed test film with the density steps of a density step tablet to determine if the test film can be matched in density with step densities corresponding to those obtainable from an operationally normal condition of the x-ray system at said same exposure technique factors, using the same filter element.

13. A method of evaluating the performace of an x-ray system as set forth in claim 12, wherein the step of comparing the density of the developed test film is carried out using an x-ray system test tool comprising housing means formed of optically opaque material having a top wall and a spaced parallel bottom wall, means defining a linear channel between said walls, an optical density step tablet slidably disposed in said linear channel and having a plurality of step segments graduated in optical density, means defining a transverse channel extending from one edge of said housing means perpendicular to and communicating with said linear channel, said transverse channel being adapted to receive a test film for comparison with said optical density step segments, means defining light-transmitting windows in said housing means simultaneously exposing said linear and transverse channels at the region where the transverse channel communicates with the linear channel, and x-ray filter means mounted on said housing means at a non-interfering location relative to said windows.

* * * * *